United States Patent [19]

Mais et al.

[11] Patent Number: 4,990,707

[45] Date of Patent: Feb. 5, 1991

[54] PROCESS FOR THE RING CHLORINATION OF AROMATIC HYDROCARBONS

[75] Inventors: Franz-Josef Mais, Duesseldorf; Helmut Fiege, Leverkusen, both of Fed. Rep. of Germany

[73] Assignee: Bayer Aktiengesellschaft, Leverkusen, Fed. Rep. of Germany

[21] Appl. No.: 427,264

[22] Filed: Oct. 26, 1989

[30] Foreign Application Priority Data

Nov. 5, 1988 [DE] Fed. Rep. of Germany ....... 3837574
Nov. 5, 1988 [DE] Fed. Rep. of Germany ....... 3837575

[51] Int. Cl.$^5$ .............................................. C07C 17/12
[52] U.S. Cl. .................................. 570/210; 570/206; 570/207; 570/208; 570/209
[58] Field of Search ..................... 570/206, 207, 208, 570/209, 210

[56] References Cited

U.S. PATENT DOCUMENTS

| | | | |
|---|---|---|---|
| 4,031,147 | 6/1977 | Graham | 570/209 |
| 4,851,596 | 7/1989 | Mais et al. | 570/209 |
| 4,925,994 | 5/1990 | Mais et al. | 570/209 |

FOREIGN PATENT DOCUMENTS

| | | | |
|---|---|---|---|
| 0126669 | 11/1984 | European Pat. Off. | 570/209 |
| 0292824 | 11/1988 | European Pat. Off. | 570/209 |

*Primary Examiner*—Werren B. Lone
*Attorney, Agent, or Firm*—Sprung Horn Kramer & Woods

[57] ABSTRACT

Aromatic hydrocarbons which are monosubstituted by straight-chain or branched $C_1$–$C_{12}$-alkyl or by $C_3$–$C_8$-cycloalkyl can be chlorinated in the presence of Friedel-Crafts Catalysts in liquid phase on the aromatic ring if cyclic benzo-fused imines or benzo[f]-1,4-thiazepines are used as co-catalysts. This makes it possible to obtain a higher proportion of p-isomers.

17 Claims, No Drawings

PROCESS FOR THE RING CHLORINATION OF AROMATIC HYDROCARBONS

BACKGROUND OF THE INVENTION

The invention relates to a process for the ring chlorination of aromatic hydrocarbons in the presence of Friedel-Crafts catalysts and in the presence of co-catalysts in liquid phase.

The reaction of aromatic hydrocarbons, such as toluene, in liquid phase with chlorine gas to give ring-substituted chlorinated derivatives, such as monochlorotoluene, is known (Ullmanns Enzyklopädie der technischen Chemie (Ullmann's Encyclopaedia of Industrial Chemistry), 4th edition, Volume 9, page 499f.). In general this chlorination is carried out in the presence of Friedel-Crafts catalysts, such as iron (III) chloride, antimony chlorides or aluminum chloride. The chlorination product obtained is usually a mixture of isomeric monochlorinated and polychlorinated compounds. If $FeCl_3$ is used, for example, a mixture of monochlorotoluenes and dichlorotoluenes is obtained from toluene; the main product of the monochlorotoluene fraction is o-chlorotoluene beside p-chlorotoluene and a small amount of m-chlorotoluene.

Since especially p-chloroalkylbenzenes, such as p-chlorotoluene, are useful intermediates, there has not been a lack of attempts in the past to control the chlorination in such a manner that the ratio of o- to p-chloroalkylbenzenes is lowered, that is, the attempt is made to find conditions which favour the formation of p-chloroalkylbenzenes.

It is known from U.S. Pat. No. 3,226,447 that by the addition of sulphur compounds having divalent sulphur to the Friedel-Crafts catalyst an o/p ratio of 1.2 can be obtained in the chlorination of toluene. The disadvantage of this process resides in the fact that this less than favourable ratio can only be achieved if antimony salts are used as Friedel-Crafts catalysts. Another disadvantage is that the required amounts of the catalyst components according to Example 16 of that application are very high, specifically 1% by weight for each of the two catalytic additives. As shown by the o/p ratio having a value of >1, the result is still more o- than p-chlorotoluene.

DE-OS (German Published Specification) No. 1,543,020 and U.S. Pat. No. 4,031,144 also describe the chlorination of toluene, for example, with $FeCl_3$ and $S_2Cl_2$. The ratio obtained of o/p=1.03–1.10 is still unsatisfactorily high.

U.S. Pat. No. 4,031,147, U.S. Pat. No. 4,069,263, U.S. Pat. No. 4,069,264 and U.S. Pat. No. 4,250,122 describe the chlorination of toluene with Friedel-Crafts catalysts with the addition of thianthrenes or substituted thianthrenes. The most favourable o/p ratios obtainable are around 0.7, which, however, are only obtained either by using antimony salts or, if iron salts are used, only at very low reaction temperatures of about 0° C. Both situations are extremely unfavourable for practical applications. Thus, the co-catalytic action of the thianthrenes in combination with the use of antimony salts is greatly impaired by traces of iron, which is difficult to realize in practice. In addition the reaction is strongly exothermic to such an extent that removal of the heat is about 0° C. by ice/salt cooling becomes very expensive. The thianthrenes are furthermore destroyed under conventional reaction conditions even by the ever-present traces of water and thus lose their efficiency.

Furthermore, U.S. Pat. No. 4,289,916, EP No. 63,384 and EP No. 173,222 disclose the chlorination of toluene in the presence of Lewis acids and phenoxathiines. The o/p ratio of 0.6 obtainable according to Example 1 from EP No. 173,222 is again achieved only by the use of antimony chloride and the high amount of 0.29% by weight of co-catalyst, which are extremely unfavourable for practical application. By using $FeCl_3$ instead of antimony chloride, an o/p ratio of 0.68 is obtained, but again only at a low reaction temperature of 5° C., which is extremely unfavourable for practical application. At a reaction temperature of 50° C., which is advantageous for practical application, the o/p ratio increases to 0.88 in the presence of $FeCl_3$ and the phenoxathiine derivative claimed in EP No. 173,222, as shown by experiments which we carried out (cf. Example 27). U.S. Pat. No. 4,289,916 and EP No. 63,384 mentioned describe a favourable o/p ratio of about 0.8. In this case, too, the o/p ratio can be lowered to 0.65 by using, instead of $FeCl_3$, antimony chloride and a reaction temperature of 20° C., that is, unfavourable conditions for practical application. In addition, phenoxathiines are destroyed in the presence of traces of water.

EP No. 126,669 discloses the chlorination of toluene in the presence of Friedel-Crafts catalysts and N-substituted phenothiazines. In this case, too, the o/p ratio of 0.84 is unfavourably high.

EP No. 112,722, EP No. 154,236 and EP No. 248,931 disclose the chlorination of toluene in the presence of certain zeolites, in which an o/p ratio of about 0.3 is achieved if, for example, halocarboxylic acid halides are added as moderators. The disadvantages of this process are the substantial amounts of 5% by weight of zeolite and 1% by weight of moderators. As our own experiments have shown, this result must be paid for by the substantial disadvantage that very large amounts (up to 8% by weight) of benzyl chlorides are formed in the mixtures obtained. The formation of benzyl chlorides interferes in the subsequent conventional workup by distillation quite extensively.

SUMMARY OF THE INVENTION

A process has now been found for the ring chlorination of aromatic hydrocarbons of the formula

in which

R denotes straight-chain or branched $C_1$–$C_{12}$-alkyl or $C_3$–$C_8$-cycloalkyl in the presence of Friedel-Crafts catalysts and in the presence of co-catalysts in liquid phase, which is characterized in that the co-catalysts used are cyclic-benzofused imines of the formula

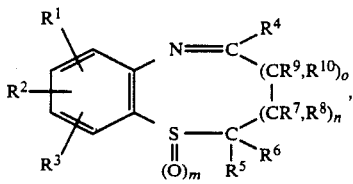

in which $R^1$ and $R^2$, independently of one another, denote hydrogen, hydroxyl, amino, cyano, halogen, nitro, carboxyl, halocarbonyl, carboxyamide, alkoxycarbonyl, alkyl, aryl, alkoxy, aryloxy, acyloxy, alkylthio, arylthio, acylthio, acyl, thioacyl or acylamino, $R^3$ represents hydrogen or chlorine and can further form a fused saturated, unsaturated or aromatic isocyclic or heterocyclic 5- to 8-membered ring with one of the radicals $R^1$ or $R^2$, if substituted adjacently and together with the substituted carbon atoms, $R^4$ denotes hydrogen, alkyl, aryl, halogen, alkylthio, arylthio, alkoxy, aryloxy, amino, hydrazino, alkylhydrazino or phenylhydrazino, m, n and o, independently of one another, can adopt the value 0 or 1 and $R^5$, $R^7$ and $R^9$, independently of one another, denote hydrogen, alkyl, alkoxy, phenyl, acyloxy, cyano, halogen, carboxyl, alkoxycarbonyl, phenoxy or acyl and $R^6$, $R^8$ and $R^{10}$, independently of one another denote hydrogen, alkyl or halogen, it being possible for $R^5$ and $R^7$ or $R^7$ and $R^9$ to represent a saturated, unsaturated or aromatic isocyclic or heterocyclic 5- 8-membered ring together with the substituted C atoms and furthermore for $R^6$ and $R^8$ or $R^8$ and $R^{10}$ together to form a double bond and furthermore for $R^5$ and $R^6$ to represent together doubly bound oxygen, sulphur or $R^{11}$—substituted nitrogen in which $R^{11}$ denotes alkyl, aryl, acyl, alkylamino or arylamino, or benzo [f]-1,4-thiazepines of the formula

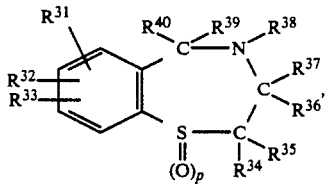

in which $R^{31}$ and $R^{32}$, independently of one another, denote hydrogen, hydroxyl, amino, cyano, halogen, nitro, $C_1$–$C_8$-alkyl, unsubstituted or $R^{31}$- and $R^{32}$-substituted phenyl (with the exception of repeated substitution by $R^{31}$-and $R^{32}$-substituted phenyl), $C_1$–$C_8$-alkoxy, phenoxy, $C_1$–$C_8$-acyloxy, $C_1$–$C_8$-acyl or $C_1$–$C_8$-alkoxycarbonyl, $R^{33}$ represents hydrogen or chlorine and can furthermore form a fused saturated, unsaturated or aromatic isocyclic or heterocyclic 5-8-membered ring with one of the radicals $R^{31}$ or $R^{32}$ and together with the substituted C atoms, $R^{34}$, $R^{36}$ and $R^{40}$, independently of one another, denote hydrogen, $C_1$–$C_8$-alkyl, unsubstituted or $R^{31}$- and $R^{32}$-substituted phenyl (with the exception of repeated substitution by $R^{31}$- and $R^{32}$-substituted phenyl), $C_1$–$C_8$-acyl, $C_1$–$C_8$-alkoxycarbonyl, cyano, halogen, carboxyl, $C_1$–$C_8$-alkoxy, $C_1$–$C_8$-alkylthio, phenylthio, benzylthio, phenoxy or $C_1$–$C_8$-acyloxy, $R^{35}$, $R^{37}$ and $R^{39}$, independently of one another, denote hydrogen, $C_1$–$C_8$-alkyl, halogen, $C_1$–$C_8$-alkoxy or $C_1$–$C_8$-alkylthio, $R^{38}$ denotes hydrogen, $C_1$–$C_8$-alkyl, unsubstituted or $R^{31}$-and $R^{32}$-substituted phenyl (with the exception of repeated substitution by $R^{31}$- and $R^{32}$-substituted phenyl), $C_1$–$C_8$-acyl, $C_1$–$C_8$-thioacyl, halogenocarbonyl or $C_1$–$C_8$-alkoxycarbonyl and p represents the number zero or one, it furthermore being possible for the substituent pairs $R^{34}$ and $R^{35}$, $R^{36}$ and $R^{37}$, and $R^{39}$ and $R^{40}$, independently of one another, to denote doubly bound oxygen, sulphur or $R^{38}$-substituted nitrogen and furthermore for the substituent pairs $R^{35}$ and $R^{36}$, and $R^{38}$ and $R^{39}$, independently of one another, to form a double bond and furthermore for the substituent pairs $R^{34}$ and $R^{37}$, and $R^{38}$ and $R^{39}$, independently of one another, to form 3- to 5-membered alkylene in which 1 or 2 C atoms can be replaced by oxygen, sulphur or $R^{38}$-substituted nitrogen and furthermore for $R^{40}$ also to adopt the meaning of hydrazino, $C_1$–$C_8$-alkylhydrazino or phenylhydrazino.

DETAILED DESCRIPTION OF THE INVENTION

The co-catalysts of the formulae (II) and (III) to be used according to the invention have the common characteristic of representing benzo-fused nitrogen-sulphur heterocycles.

Examples of halogens are fluorine, chlorine, bromine or iodine, preferably fluorine, chlorine or bromine, particularly preferably fluorine or chlorine.

Suitable alkyl radicals in the substituents mentioned are open-chain radicals having 1–16 carbon atoms, preferably 1–8 carbon atoms, particularly preferably 1–4 carbon atoms, and cyclic radicals having 5–8 carbon atoms, preferably 5 or 6 carbon atoms. These alkyl radicals can themselves be substituted by $C_1$–$C_4$-alkyl, preferably methyl or ethyl, thus arriving at the series of branched alkyl radicals. These alkyl radicals can furthermore be monosubstituted or polysubstituted by fluorine, chlorine or bromine. These alkyl radicals can furthermore be substituted by $C_1$–$C_4$-alkoxy, preferably methoxy or ethoxy, thus arriving at the ether series. These alkyl radicals can furthermore be substituted by phenyl, naphthyl or biphenyl, thus arriving at the series of aralkyl radicals. Examples of such alkyl radicals are: methyl, ethyl, propyl, isopropyl, butyl, isobutyl, tert. butyl, amyl, hexyl, octyl, decyl, dodecyl, hexadecyl, cyclopentyl, methylcyclopentyl, cyclohexyl, methylcyclohexyl, cycloheptyl, cyclooctyl, methoxymethyl, ethoxymethyl, benzyl, phenylethyl, chloromethyl, dichloromethyl, trichloromethyl, trifluoromethyl; particularly important radicals are, for example, methyl, ethyl, n-propyl, benzyl and trifluoromethyl.

The range of meaning mentioned for alkyl radicals applies in principle also to alkoxy and alkylthio as well as, in a corresponding manner, to acyl and acyloxy; radicals having 1–6 carbon atoms are preferred, those having 1–4 carbon atoms, such as methoxy, ethoxy, tert. butoxy, cyclohexyloxy, trifluromethoxy, methylthio, ethylthio, cyclohexylthio, trifluromethylthio, trichloromethylthio, formyl, acetyl, propionyl, acetyloxy, propionyloxy, trichloroacetyl, trifluoroacetyl, benzoyl, chlorobenzoyl, chloroacetyl and the like are particularly preferred.

Examples of suitable aryl radicals in the above substituents are phenyl, naphthyl or biphenyl, which themselves can be substituted by fluorine, chlorine, bromine, nitro, $C_1$–$C_4$-alkyl or $C_1$–$C_4$-alkoxy, for example phenyl, naphthyl, tolyl, anisyl, chlorophenyl, nitrophenyl; for example, phenyl and chlorophenyl are particularly important.

What has been said above with respect to the alkoxy and alkylthio radicals applies analogously to the aryloxy and arylthio radicals. In the case where $R^3$ forms a ring with one of the radicals $R^1$ or $R^2$ and together with the substituted carbon atoms, this ring can be isocyclic and saturated, unsaturated or aromatic or even be heterocyclic by containing N, O and/or S atoms.

Rings of this type have 5–8, preferably 5 or 6, ring members and are fused onto the benzene ring shown in formula (III). Examples are: benzo, naphthalino, thieno, furano, pyrrolo, pyridino, cyclohexano, cyclopentano, oxolano, dioxolano, and preferably benzo and cyclohexano.

In the case where $R^{33}$ forms a ring with one of the radicals $R^{31}$ or $R^{32}$ and together with the substituted C atoms, this ring can be isocyclic and saturated, unsaturated or aromatic or even be heterocyclic by containing N, O and/or S atoms. These rings have 5–8, preferably 5 or 6 ring members and are fused to the benzene ring shown in formula (III). Examples are: benzo, naphthalino, thieno, furano, pyrrolo, pyridino, cyclohexano, cyclopentano, oxolano, dioxolano, preferably benzo and cyclohexano.

$C_1$–$C_8$-thioacyl is derived from $C_1$–$C_8$-acyl by replacing oxygen by sulphur.

Halogenocarbonyl can be fluorocarbonyl, chlorocarbonyl or bromocarbonyl, preferably chlorocarbonyl.

The substituent pairs mentioned in detail can, independently of one another, denote doubly bound oxygen, sulphur or $R^{38}$-substituted nitrogen, the double bonds mentioned in detail or 3- to 5-membered alkylene, which in the latter case makes it possible to form fused cycloaliphatic rings which if fused at the 2- and 3-position of the skeleton according to formula (III) can also contain an olefinic bond. Furthermore, these fused rings can be non-aromatic heterocyclic rings if 1 or 2 C atoms in the alkylene chain are replaced by oxygen, sulphur or $R^{38}$-substituted nitrogen.

The cyclic benzo-fused imines of the formula (II) to be used according to the invention as co-catalysts are characterized by the C atom connected to the N atom by a double bond and substituted by $R^4$. A single bond or 1 or 2 further C atoms as defined with respect to index o and n can be inserted between this C atom just mentioned and the C atom which is adjacent to the S atom. Thus, formula (II) includes cyclic benzo-fused imines whose ring system can be 6-,7- or 8-membered and can be represented by the following formulae:

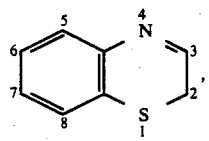
(IIa)

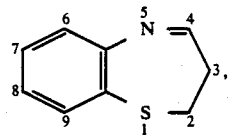
(IIb)

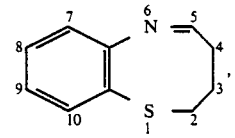
(IIc)

Formulae (IIa), (IIb) and (IIc) show the numbering of the atoms forming the ring structure, while the possible substituents have been omitted for reasons of clarity.

A list of co-catalysts usable according to the invention, which is by no means exhaustive, is as follows:
3-methylthio-2H-1,4-benzothiazine,
3-benzylthio-2H-1,4-benzothiazine,
3-methoxy-2H-1,4-benzothiazine,
2-methyl-3-methylthio-2H-1,4-benzothiazine,
3-ethylthio-2H-1,4-benzothiazine-2-one,
3-acetylthio-2H-1,4-benzothiazine,
2-phenyl-3-methylthio-2H-1,4-benzothiazine,
3-methylthio-6-methyl-2H-1,4-benzothiazine,
3-methylthio-6-chloro-2H-1,4-benzothiazine,
3-methylthio-7-chloro-2H-1,4-benzothiazine,
5,7-dichloro-3-ethylthio-2H-1,4-benzothiazine,
6,8-dimethyl-3-methylthio-2H-1,4-benzothiazine,
7-trifluoromethyl-3-methoxy-2H-1,4-benzothiazine,
7-trifluoromethyl-3-methylthio-2H-1,4-benzothiazine,
5,7-dichloro-2,6-dimethyl-3-methylthio-2H-1,4-benzothiazine,
3-ethoxy-2H-1,4-(2,3-naphthaleno)thiazene,
3,6-dimethoxy-2H-1,4-benzothiazine,
6-methoxy-3-propylthio-2H-1,4-benzothiazine,
3-methylthio-6-methoxy-2H-1,4-benzothiazine,
3-methylthio-1-oxo-2H-1,4-benzothiazine,
4-methylthio-2,3-dihydro-1,5-benzothiazepine,
6,8-dichloro-4-methylthio-2,3-dihydro-1,5-benzothiazepine,
7-trifluoromethyl-4-methylthio-2,3-dihydro-1,5-benzothiazepine,
8-methoxy-4-methylthio-2,3-dihydro-1,5-benzothiazepine,
7-methoxy-4-methylthio-2,3-dihydro-1,5-benzothiazepine,
4-methoxy-2,3-dihydro-1,5-benzothiazepine,
4-methylthio-1,5-benzothiazepin-2(3H)-one;
4-ethylthio-2,3-dihydro-1,5-benzothiazepine,
4-methyl-2,3-dihydro-1,5-benzothiazepine,
2,2,4-trimethyl-2,3-dihydro-1,5-benzothiazepine,
4-methyl-2,3-tetramethylene-1,5-benzothiazepine,
4-phenylhydrazino-2,3-dihydro-1,5-benzothiazepine,
4-methylthio-7,9-dimethyl-2,3-dihydro-1,5-benzothiazepine,
4-benzylthio-2,3-dihydro-1,5-benzothiazepine,
4-methylthio-7,8-dimethyl-2,3-dihydro-1,5-benzothiazepine,
2-methyl-4-methylthio-2,3-dihydro-1,5-benzothiazepine,
2,3-dimethyl-4-methylthio-2,3-dihydro-1,5-benzothiazepine,
2,3-tetramethylene-4-methylthio-2,3-dihydro-1,5-benzothiazepine,
2,3-trimethylene-4-methylthio-2,3-dihydro-1,5-benzothiazepine,
7-methoxy-4-methylthio-2,3-tetramethylene-2,3-dihydro-1,5-benzothiazepine,
7,8-dimethyl-4-methylthio-2,3-tetramethylene-2,3-dihydro-1,5-benzothiazepine, 7,9-dimethyl-4-methylthio-2,3-tetramethylene-2,3-dihydro-1,5-benzothiazepine,
2,3-tetramethylene-4-methoxy-2,3-dihydro-1,5-benzothiazepine,
7,9-dimethyl-4-methoxy-2,3-tetramethylene-2,3-dihydro-1,5-benzothiazepine,
6,8-dichloro-7-methyl-4-methylthio-2,3-dihydro-1,5-benzothazepine,
7-chloro-4-methoxy-2,3-dihydro-1,5-benzothiazepine,
4-methylthio-1-oxo-2,3-dihydro-1,5-benzothiazepine,
2-phenyl-4-methylthio-2,3-dihydro-1,5-benzothiazepine,
4,7,8-trimethoxy-2-phenyl-2,3-dihydro-1,5-benzothiazepine,
8,9-dichloro-7-methyl-4-methoxy-2,3-trimethylene-2,3-dihydro-1,5-benzothiazepine,
2-methyl-4-methylthio-1,5-benzothiazepine,
4-methylthio-1,5-benzothiazepine,
4-methylthio-1,5-dibenzo-[b,f]thiazepine,
2,3-dichloro-4-methylthio-1,5-benzothiazepine,
7,8-dimethyl-2-phenyl-4-methoxy-2,3-dihydro-1,5-benzothiazepine,
3-acetoxy-4-methylthio-2,3-dihydro-1,5-benzothiazepine,
3-acetamido-4-methylthio-2,3-dihydro-1,5-benzothiazepine,
2-propyl-4-methylthio-2,3-dihydro-1,5-benzothiazepine,
2-propyl-4-propylthio-2,3-dihydro-1,5-benzothiazepine,
4-methylthio-1,5-(1,2-naphthaleno)thiazepine,
4-methoxy-1,5-benzothiazepine,
4-acetylthio-2,3-dihydro-1,5-benzothiazepine,
2,3-dimethyl-4-acetyl-2,3-dihydro-1,5-benzothiazepine,
4-propionylthio-2,3-dihydro-1,5-benzothiazepine,
4-propionyloxy-2,3-dihydro-1,5-benzothiazepine,
4-chlorocarbonylthio-2,3-dihydro-1,5-benzothiazepine,
4-benzoylthio-2,3-dihydro-1,5-benzothiazepine,
7,9-dimethyl-4-acetyloxy-2,3-dihydro-1,5-benzothiazepine,
5-methylthio-3,4-dihydro-2H-1,6-benzothiazocine,
2-methyl-5-methylthio-3,4-dihydro-2H-1,6-benzothiazocine,
2-phenyl-5-methylthio-3,4-dihydro-2H-1,6-benzothiazocine,
5-methoxy-2H-3,4-dihydro-1,6-benzothiazocine,
8,10-dimethyl-5-methylthio-2H-3,4-dihydro-1,6-benzothiazocine,
5-methylthio-2,3-tetramethylene-2H-3,4-dihydro-1,6-benzothiazocine,
2,3-dimethyl-5-methylthio-2H-3,4-dihydro-1,6-benzothiazocine,
5-ethylthio-2H-3,4-dihydro-1,6-benzothiazocine,
5-methylthio-2H-3,4-dihydro-1,6-benzothiazocin-2-one,
8-methoxy-5-methylthio-2H-3,4-dihydro-1,6-benzothiazocine,
5-methylthio-2H-1,6-dibenzo[c,g]thiazocine,
5-methylthio-3,4-tetramethylene-2H-3,4-dihydro-1,6-benzothiazocine,
5-methylthio-1-oxo-2H-3,4-dihydro-1,6-benzothiazocine,
7,9-dichloro-5-ethoxy-2H-3,4-dihydro-1,6-benzothiazocine,
2-chloro-5-methylthio-4H-1,6-benzothiazocine,
5-methylthio-2H-3,4-dihydro-1,6-benzothiazocine-2-thione,
5-methylthio-4H-1,6-dibenzo[b,g]thiazocine,
5-methoxy-8-trifluoromethyl-2H-3,4-dihydro-1,6-benzothiazocine,
4-methyl-5-ethylthio-2H-3,4-dihydro-1,6-benzothiazocine,
5-methylthio-2H-1,6-benzothiazocin-2-one,
5-methylthio-2H-3,4-dihydro-1,6(1,2-naphthaleno)thiazocine, preferred are:
4-methylthio-2,3-dihydro-1,5-benzothiazepine,
6,8-dichloro-4-methylthio-2,3-dihydro-1,5-benzothiazepine,
7-trifluoromethyl-4-methylthio-2,3-dihydro-1,5-benzothiazepine,
7-methoxy-4-methylthio-2,3-dihydro-1,5-benzothiazepine,
4-methylthio-7,9-dimethyl-2,3-dihydro-1,5-benzothiazepine,
4-methylthio-7,8-dimethyl-2,3-dihydro-1,5-benzothiazepine,
2-methyl-4-methylthio-2,3-dihydro-1,5-benzothiazepine,
2,3-dimethyl-4-methylthio-2,3-dihydro-1,5-benzothiazepine,
2,3-tetramethylene-4-methylthio-2,3-dihydro-1,5-benzothiazepine,
2,3-trimethylene-4-methylthio-2,3-dihydro-1,5-benzothiazepine,
7-methoxy-4-methylthio-2,3-tetramethylene-2,3-dihydro-1,5-benzothiazepine,
7,8-dimethyl-4-methylthio-2,3-tetramethylene-2,3-dihydro-1,5-benzothiazepine,
4-methyl-2,3-dihydro-1,5-benzothiazepine,
4-methyl-2,3-tetramethylene-2,3-dihydro-1,5-benzothiazepine,
4-phenylhydrazino-2,3-dihydro-1,5-benzothiazepine,
7,9-dimethyl-4-methylthio-2,3-tetramethylene-2,3-dihydro-1,5-benzothiazepine,
7,9-dimethyl-4-methoxy-2,3-tetramethylene-2,3-dihydro-1,5-benzothiazepine,
8,9-dichloro-7-methyl-4-methoxy-2,3-trimethylene-2,3-dihydro-1,5-benzothiazepine,
2-propyl-4-methylthio-2,3-dihydro-1,5-benzothiazepine,
4-acetylthio-2,3-dihydro-1,5-benzothiazepine.

Preferred cyclic benzo-fused imines usable according to the invention are those of the formulae

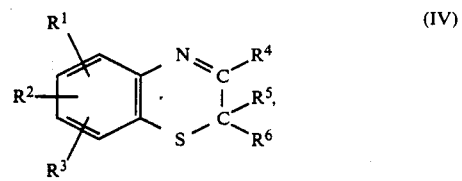

(IV)

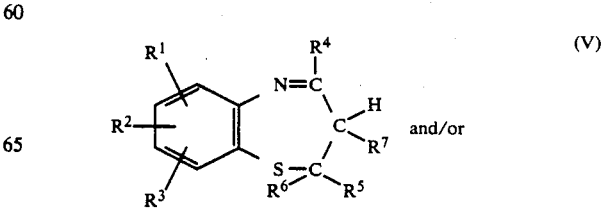

(V)

and/or

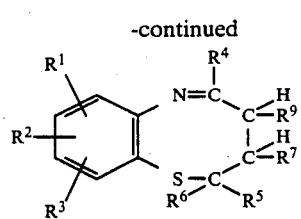

(VI)

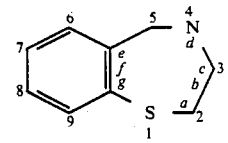

1,4-thiazepine system and whose basic structure, showing the atomic positions and bonds, is as follows:

In the formulae (IV), (V) and (VI) of these preferred co-catalysts, $R^1$ to $R^9$ have the abovementioned range of meanings.

Particularly preferred co-catalysts are those of the formulae (IV), (V) and (VI) in which the radicals $R^{12}$, $R^{13}$ and $R^{14}$ take the place of $R^1$, $R^2$ and $R^3$, in which $R^{12}$ and $R^{13}$, independently of one another, denote hydrogen, halogen, nitro, alkyl, aryl, alkoxy, aryloxy, acyloxy, alkylthio, arylthio or acyl and $R^{14}$ represents hydrogen or chlorine and furthermore can form a fused, saturated isocyclic 5-7-membered ring or a fused benzene ring with one of the radicals $R^{12}$ or $R^{13}$ and together with the C atoms substituted by them.

Very particularly preferably, co-catalysts of the formulae (IV), (V) and (VI) are used in which the radicals $R^{21}$, $R^{22}$ and $R^{23}$ take the place of $R^{12}$, $R^{13}$ and $R^{14}$, of which $R^{21}$ and $R^{22}$, independently of one another, denote hydrogen, $C_1-C_4$-alkyl, $C_1-C_4$-alkoxy, fluorine or chlorine and $R^{23}$ represents hydrogen or chlorine and furthermore can form a fused benzene ring with one of the radicals $R^{21}$ or $R^{22}$ and together with the C atoms substituted by them.

Further co-catalysts usable according to the invention are those of the formula (IV), (V) and (VI) in which the radical $R^{15}$ takes the place of $R^4$ and denotes hydrogen, $C_1-C_4$-alkyl, $C_1-C_4$-alkoxy, phenyl, $C_1-C_4$-acyl, $C_1-C_4$-alkylthio, benzyl, benzyloxy, benzylthio, hydrazino, $C_1-C_4$-alkylhydrazino, phenylhydrazino or chlorine.

Co-catalysts of the formulae (IV), (V) and (VI) in which the radical $R^{24}$ takes the place of $R^{15}$ and denotes hydrogen, $C_1-C_4$-alkyl, benzyl, phenyl, $C_1-C_4$-alkoxy, $C_1-C_4$-alkylthio, benzyloxy, benzylthio, hydrazino or phenylhydrazino are particularly preferred.

Further preferred co-catalysts usable according to the invention are those of the formulae (IV), (V) and (VI) in which the radicals $R^{16}$, $R^{17}$, $R^{18}$ and $R^{19}$ take the place of $R^5$, $R^6$, $R^7$ and $R^9$ and, independently of one another, denote hydrogen, $C_1-C_4$-alkyl, fluorine or chlorine, it being possible for $R^{16}$, $R^{18}$ and $R^{19}$ additionally to denote $C_1-C_4$-alkoxy, $C_1-C_4$-acyl or phenyl and furthermore to form, if substituted adjacently, a cyclopentane, cyclohexane or benzene ring together with the substituted C atoms.

In a particularly preferred manner, cyclic benzo-fused imines of the formula (V) are used.

The cyclic benzo-fused imines to be used according to the invention can be prepared by processes known per se. For example, cyclic thioamides can be metallated and reacted to imines by means of electrophilic reagents (Chem. Ber. 102, 1869 (1969), J. Heterocyclic Chem. 20, 1593 (1985)). Furthermore, o-aminothiophenols can be reacted directly with a,b-unsaturated ketenes or dimeric ketenes to cyclic imines (U.S. Pat. No. 3,125,563, Chem. Ber. 90, 2683 (1957), Khim. Geterotsikl. Soedin 1968, 468).

The other usable co-catalysts of the formula (III) are compounds which are benzo-fused at the [f]-bond of the The list which follows and is by no means exhaustive serves as illustration of such benzo[f]-1,4-thiazepins:
4-acetyl-2,3-dihydro-1,4-benzothiazepin-5-(4H)-one
4-chlorocarbonyl-2,3-dihydro-1,4-benzothiazepin-5(4H)-one
5-methoxy-2,3-dihydro-1,4-benzothiazepine
2,3-dimethyl-2,3-dihydro-5-methoxy-1,4-benzothiazepine
2,3,5-trimethyl-2,3-dihydro-1,4-benzothiazepine
2,3-dihydro-1,4-benzothiazepin-5(4H)-one-1-oxide
2,3-dihydro-1,4-benzothiazepine-5(4H)-thione
2,3-dihydro-1,4-benzothiazepin-5(4H)-one
4-methyl-2,3-dihydro-1,4-benzothiazepin-5(4H)-one
2,3-tetramethylene-2,3-dihydro-1,4-benzothiazepin-5(4H)-one
2,3-tetramethylene-2,3,4,5-tetrahydro-1,4-benzothiazepine
4-ethyl-2,3,4,5-tetrahydro-1,4-benzothiazepine
2,4-dimethyl-2,3,4,5-tetrahydro-1,4-benzothiazepine
7-methoxy-2,3-tetramethylene-2,3-dihydro-1,4-benzothiazepin-5(4H)-one
7,9-dimethyl-2,3-tetramethylene-2,3-dihydro-1,4-benzothiazepin-5(4H)-one
2,3-tetramethylene-4-methylthio-2,3-dihydro-1,4-benzothiazepine
7,9-dimethyl-2,3-tetramethylene-4-methyl-thio-2,3-dihydro-1,4-benzothiazepine
2-phenylthio-2,3-dihydro-1,4-benzothiazepin-5(4H)-one
5-ethylthio-2,3-dihydro-1,4-benzothiazepine
5-methylthio-2,3-dihydro-1,4-benzothiazepine
5-benzylthio-2,3-dihydro-1,4-benzothiazepine
5-methyl-2,3-dihydro-1,4-benzothiazepine
3-acetyloxy-2,3-dihydro-1,4-benzothiazepin-5(4H)-one
2,3-dimethyl-7-nitro-2,3-dihydro-1,4-benzothiazepin-5(4H)-one
4-chlorocarbonyl-2,3,4,5-tetrahydro-1,4-benzothiazepine
1,4-benzothiazepine-2(3H)-5(4H)-dione
1,4-benzothiazepine-2(3H)-5(4H)-dithione
4-acetyl-2,3-tetramethylene-2,3,4,5-tetrahydro-1,4-benzothiazepine
5,7-dimethoxy-2,3-dihydro-1,4-benzothiazepin-5(4H)-one
7-methylthio-2,3-dihydro-1,4-benzothiazepin-5(4H)-one
7,8-dimethylthio-2,3-dihydro-1,4-benzothiazepin-5(4H)-one
7,8-tetramethylene-2,3-dihydro-1,4-benzothiazepin-5(4H)-one
5-methyl-2,3-dihydro-1,4-benzothiazepin-1-oxide
2-methyl-2,3-dihydro-1,4-benzothiazepin-5(4H)-one
2,7,9-trimethyl-2,3-dihydro-1,4-benzothiazepin-5(4H)-one
2,7,9-trimethyl-5-methoxy-2,3-dihydro-1,4-benzothiazepine
2,7,9-trimethyl-5-b-phenylhydrazino-2,3-dihydro-1,4-benzothiazepine
3-methyl-2,3-dihydro-1,4-benzothiazepin-5(4H)-one 7,9-dimethyl-8-chloro-2,3-dihydro-1,4-benzothiazepin-5-(4H)-one
8-trifluoromethyl-2,3-dihydro-1,4-benzothiazepin-5(4H)-one
7,8-dimethyl-4-trifluoroacetyl-2,3-dihydro-1,4-benzothiazepin-5(4H)-one
2-acetyl-2,3-dihydro-1,4-benzothiazepin-5(4H)-one
5-b-phenylhydrazino-2,3-dihydro-1,4-benzothiazepine
2-chloro-2,3-dihydro-1,4-benzothiazepin-5(4H)-one
2-chloro-1,4-benzothiazepin-5(4H)-one
3-methyl-1,4-benzothiazepin-5(4H)-one
3,7,9-trimethyl-1,4-benzothiazepin-5(4H)-one
7-methyl-2,3-dihydro-1,4-benzothiazepin-5(4H)-one
7-methyl-8-chloro-2,3-dihydro-1,4-benzothiazepin-5(4H)-one
4-acetyl-2,3,4,5-tetrahydro-1,4-benzothiazepine
2,3,4,5-tetrahydro-1,4-benzothiazepine
2,3-dimethyl-2,3,4,5-tetrahydro-1,4-benzothiazepine
7,9-dichloro-2,3-dihydro-1,4-benzothiazepin-5(4H)-one
7-nitro-2,3-dihydro-1,4-benzothiazepin-5(4H)-one
8-cyano-2,3-dihydro-1,4-benzothiazepin-5(4H)-one
8-chloro-2,3-dihydro-1,4-benzothiazepin-5(4H)-one
7,9-dibromo-2,3-dihydro-1,4-benzothiazepin-5(4H)-one
3-acetyl-2,3-dihydro-1,4-benzothiazepin-5(4H)-one
2-phenyl-3-methyl-2,3-dihydro-1,4-benzothiazepin-5(4H)-one
4-methoxy-7-methyl-2,3-dihydro-1,4-benzothiazepine
4-b-phenylhydrazino-7-methyl-2,3-dihydro-1,4-benzothiazepine Preferred benzo[f]-1,4-thiazepines are those in which the substituent pair $R^{39}$ and $R^{40}$ denotes doubly bound oxygen, sulphur or $R^{38}$-substituted nitrogen and the remaining substituents and symbols have the abovementioned ranges. These co-catalysts can be represented by the formula

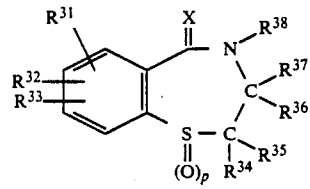 (VII)

in which

X denotes doubly bound oxygen, sulphur or $R^{38}$-substituted nitrogen and $R^{31}$ to $R^{38}$ and the index p have the abovementioned range.

In a further preferred manner, co-catalysts are used in which the substituent pair $R^{38}$ and $R^{39}$ represents a double bond and, at the same time, the substituent $R^{40}$ in a very preferred manner adopts the range of $R^{41}$. These co-catalysts can be represented by the formula

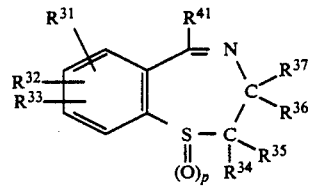 (VIII)

in which $R^{41}$ denotes $C_1$–$C_8$-alkyl, $C_1$–$C_8$-alkoxy, $C_1$–$C_8$-alkylthio, hydrazino, b-phenylhydrazino or b-$C_1$–$C_8$-alkyl-hydrazino and $R^{31}$ to $R^{37}$ and the index p have the abovementioned range of meanings.

Further preferred co-catalysts are those in which the substituent pair $R^{34}$ and $R^{37}$ denotes 3- to 5-membered alkylene and thus formed a fused 5- to 7-membered ring. These co-catalysts can be represented by the formula

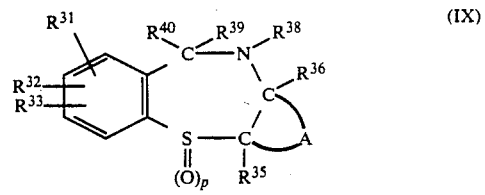 (IX)

in which

A denotes trimethylene, tetramethylene or pentamethylene and $R^{31}$, $R^{32}$, $R^{33}$, $R^{35}$, $R^{36}$, $R^{38}$, $R^{39}$, $R^{40}$ and p have the abovementioned range of meanings.

In a further preferred manner, co-catalysts are used in which the index p adopts the value zero. They can be represented by the formula

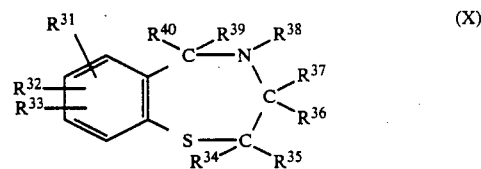 (X)

in which the radicals $R^{31}$ to $R^{40}$ adopt the abovementioned range of meanings.

In a further preferred manner, co-catalysts of the formula (III) are used in which the radicals $R^{42}$, $R^{43}$ and $R^{44}$ take the place of $R^{31}$, $R^{32}$ and $R^{33}$, of which $R^{42}$ and $R^{43}$, independently of one another, denote hydrogen, halogen, nitro, alkyl, aryl, alkoxy, aryloxy, acyloxy, alkylthio, arylthio, acyl or thioacyl and $R^{44}$ represents hydrogen or chlorine and furthermore can form a fused saturated isocyclic 5-7-membered ring or a fused benzene ring with one of the radicals $R^{42}$ and $R^{43}$ and together with the substituted C atoms.

In a very particularly preferred manner, co-catalysts of the formula (III) are used in which the radicals $R^{51}$, $R^{52}$ and $R^{53}$ take the place of $R^{42}$, $R^{43}$ and $R^{44}$, of which $R^{51}$ and $R^{52}$, independently of one another, denote hydrogen, $C_1$–$C_4$-alkyl, $C_1$–$C_4$-alkoxy, fluorine or chlorine and $R^{53}$ represents hydrogen or chlorine and furthermore can form a fused cyclopentane, cyclohexane or benzene ring with one of the radicals $R^{51}$ or $R^{52}$ and together with the substituted C atoms.

The benzo[f]-1,4-thiazepines to be used according to the invention as co-catalysts can be prepared by known processes, for example by reaction of o-mercaptobenzoic esters with substituted or unsubstituted ethyleneimine or by reaction of o-mercaptobenzoic acids with b-aminoalcohol sulphates and subsequent ring closure.

Examples of the aromatic hydrocarbons of the formula (I) to be chlorinated on the ring according to the invention are: toluene, ethylbenzene, propylbenzene, cumene, tert.-butylbenzene and phenylcyclohexane; the process is particularly important for the ring chlorination of toluene.

The process according to the invention is carried out in liquid phase, in which the aromatic hydrocarbon can be used in liquid (melted) form or, if desired, diluted with an inert solvent. Suitable solvents are those which are not attacked by chlorine under the conditions of a ring chlorination and are known to one skilled in the art, for this behaviour, such as methylene chloride, chloroform, carbon tetrachloride and acetic acid. Preferably, no solvent is used.

The chlorinating agent for the process according to the invention is preferably chlorine. The chlorine can be passed into the reaction mixture as a liquid or a gas. Preferably, gaseous chlorine is used. However, it is also possible to use other chlorinating agents which, such as, for example, sulphuryl chloride, release chlorine under the reaction conditions.

The ring chlorination to be carried out according to the invention can in principle be carried out at a temperature from the solidification point to the boiling point of the reaction mixture. In general the reaction temperature is 0°-100° C., preferably 20°-80° C., particularly preferably 40°-60° C.

The reaction pressure can be atmospheric, reduced or superatmospheric pressure and is in principle not critical. Operation at atmospheric pressure is preferred because of the low costs. Superatmospheric pressure may be advisable, for example, if the reaction is carried out above the boiling point of a low-boiling solvent; in this case, it is possible, for example, to carry out the reaction under the automatically resulting internal pressure of the reaction mixture. The chlorination degree of the reaction mixture is preferably not higher than 1, relative to the aromatic hydrocarbon to be chlorinated. Higher chlorination degrees are possible, but usually not advantageous, since they lead to the formation of undesired polychlorinated products. Chlorine or a chlorine-releasing substance is therefore used, for example, in an amount of 0.8-1.1, preferably 0.8-1.0, mole per mole of the aromatic hydrocarbon.

Friedel-Crafts catalysts for the process according to the invention are all those known, for example antimony chlorides, antimony oxychloride, aluminium chloride, iron(II) chloride, iron(III) chloride, tellurium chlorides, molybdenum chlorides, tungsten chlorides, titanium chlorides, zinc chloride, tin chlorides, boron chloride and/or boron trifluoride. However, it is also possible to use elements and compounds of elements which form a Friedel-Crafts catalyst (Lewis acid) during the chlorination. For example, the elemental metals or the semi-metals antimony, iron, lead, tin, zinc, molybdenum, tellurium and aluminium or their oxides, sulphides, carbonyls or salts,(for example carbonates or the like); examples are antimony oxides, iron oxides, iron sulphides, lead sulphides, tin sulphides, zinc sulphides, iron carbonyls, molybdenum carbonyls and/or boron phosphate. Instead of the chlorides mentioned, the bromides, optionally also the fluorides or iodides, of the elements mentioned can be used. Preferred Friedel-Crafts catalysts are antimony chlorides, aluminium chlorides, iron, iron oxides, iron sulphides, iron carbonyls and/or iron(III) chloride. Iron (III) chloride is particularly preferred.

The amounts of the Friedel-Crafts catalyst or a mixture of several of them can be varied within wide limits. Thus, a catalytic effect is already detectable with an addition of 0.0005% by weight; on the other hand, it is also possible to add 5% by weight or more of the Friedel-Crafts catalyst, but such large amounts usually do not offer any advantage, and instead may lead to difficulties during the workup. Usually the Friedel-Crafts catalyst is used in an amount of 0.001-0.5% by weight, preferably 0.01-0.1% by weight. All amounts stated are based on the amount of the aromatic hydrocarbon used.

The catalysts usable according to the invention comprise, in addition to the abovementioned substances, all substances which are capable under the reaction conditions of forming compounds or mixtures of compounds which are covered by the abovementioned formulae (II) to (X). They are, for example, those compounds which are monounsaturated or polyunsaturated in the heterocyclic ring. Furthermore, they are open-chain precursors which undergo ring closure under the conditions according to the invention and thus are converted into co-catalysts according to the invention. Furthermore, all substances which can be formed under the reaction conditions of chlorination by reaction of the abovementioned co-catalysts according to the invention with chlorine or hydrogen chloride can be used. Examples are the hydrochlorides of the abovementioned co-catalysts.

It is furthermore possible to use the co-catalysts in combination with other elements or compounds which are not claimed as co-catalysts in the process according to the invention. The co-catalysts can be used not only individually but also in a mixture of several of them. The amounts in which the co-catalysts according to the invention can be used can vary within wide limits. However, amounts under 0.0001% by weight are less advantageous, since in this case the co-catalytic action diminishes. It is even possible to add amounts of 5% by weight or more of co-catalyst, but these large amounts in general do not offer any advantage and instead may lead to difficulties during the workup. The co-catalysts according to the invention are therefore in general used in an amount of 0.0001-0.5% by weight, preferably 0.0005-0.1% by weight, particularly preferably 0.0005-0.0075% by weight, relative to the aromatic hydrocarbon used.

The molar ratio of the mixture of Friedel-Crafts catalyst(s) and co-catalyst(s) can be varied within wide limits in the process according to the invention. In general it is advantageous not to use too large an excess of the co-catalyst with respect to the Friedel-Crafts catalyst. Likewise it is in general more advantageous not to choose a too large excess of the Friedel-Crafts catalyst. According to the invention, the molar ratio of Friedel-Crafts catalyst to co-catalyst is 100:1-1:10, preferably 75:1-1:4, particularly preferably 50:1-1:2.

The water content of the reaction mixture is in principle not critical as long as the Friedel-Crafts catalyst used is not completely deactivated. Therefore, it is preferred not especially to dry the substances used but to use them in the condition in which they are usually present in industrial chemistry practice. However, it is also possible according to the invention to dry some or all of the substances used. In general, the water content should not be above the saturation limit of the substances used. Preferably, the water content of the reaction mixture is up to 250 ppm, particularly preferably up to 150 ppm, very particularly preferably up to 100 ppm.

When the process according to the invention is carried out in practice, the individual components of the reaction mixture are added in any desired order. This process can be carried out both continuously and batchwise. An exemplary embodiment is as follows:

The desired aromatic hydrocarbon, for example toluene, is initially introduced and brought to the desired temperature (for example 50° C.). The desired amounts of Friedel-Crafts catalyst(s) and co-catalyst(s) are added in any desired order and, while keeping the temperature essentially constant, chlorine gas is introduced until the desired chlorination degree has been reached. The mixture is then worked up in a conventional manner by distillation.

A further exemplary embodiment is as follows:

A mixture of alkylbenzene containing the desired amounts of catalyst and co-catalyst is prepared and brought to the desired reaction temperature. The chlorinating agent is then introduced until the desired chlorination degree has been reached. The workup can in this case also be carried out in a conventional manner by distillation.

A further embodiment is as follows:

A solution of catalyst and co-catalyst in the alkylbenzene is prepared and transferred to a continuously operating chlorinating apparatus. Likewise a chlorinating agent is introduced continuously at such a rate that the desired chlorination degree is reached. In this case, too, the reaction mixture being formed continuously can be worked up in a conventional manner by distillation.

In contrast to the process according to the invention, the previously known heterocycles for controlling the o/p selectivity always had a different structure, that is to say, the form of three linearly fused 6-membered rings.

In the process according to the invention, it is surprising that the co-catalysts according to the invention have such a distinct selecting effect on the o/p ratio, with the result that predominantly the p-compound is formed. Furthermore, the fact that the co-catalysts according to the invention yield such good results especially in combination with the Friedel-Crafts catalyst FeCl$_3$ which is extremely favourable and desirable for practical application is particularly surprising and extremely advantageous. The o/p ratio of o/p=0.55 achieved, for example, for toluene is the lowest so far achieved by using combinations of Friedel-Crafts catalysts and co-catalysts.

Another surprising fact is that these good results are achieved at temperatures, for example in the range of 40°-60° C., which are very advantageous in terms of practical application. Still another surprising fact is that the co-catalysts according to the invention exhibit their p-selective action even at extremely low concentrations, so that the required amounts of co-catalysts are particularly small. Thus, they are in the particularly preferred range of 0.0005–0.0075% by weight, which is powers of ten less than in the case of the previously known co-catalysts.

This fact is extremely advantageous in terms of practical application as well as in economical and ecological terms. The examples which follow illustrate the invention without limiting it thereto.

EXAMPLE 1

100 parts by weight of toluene were initially introduced into a reactor with stirring, and 0.017 part by weight of FeCl$_3$ and 0.0047 part by weight of the co-catalyst of the formula

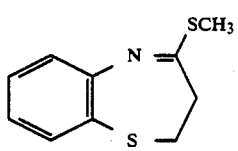

(4-methylthio-2,3-dihydro-1,5-benzothiazepin)

was added and the mixture was heated to 50° C. While maintaining the temperature essentially constant (±1° C.), about 94 mol % of chlorine (based on toluene) was uniformly introduced as a gas over a period of 5 hours. The residual toluene content in the reaction mixture was 3.8% by weight and the ratio of ortho-chlorotoluene to para-chlorotoluene (o/p) was 0.71.

EXAMPLE 2

The procedure of Example 1 was repeated. However, 0.0050 part by weight of the co-catalyst of the formula

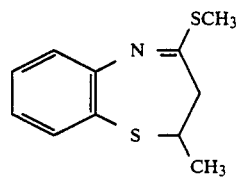

(2-methyl-4-methylthio-2,3-dihydro-1,5-benzothiazepine)

was added. The residual toluene content was 2.7% by weight and the o/p ratio 0.71.

EXAMPLE 3

The procedure of Example 1 was repeated. However, 0.0064 part by weight of the co-catalyst of the formula

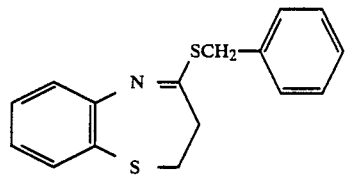

(4-benzylthio-2,3-dihydro-1,5-benzothiazepine)

was added. The residual toluene content was 4.6% and the o/p ratio 0.86.

EXAMPLE 4

The procedure of Example 1 was repeated. However, 0.0045 part by weight of the co-catalyst of the formula

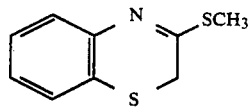

(3-methylthio-2H-1,4-benzothiazine)

was added. The residual toluene content was 4.1% by weight and the o/p ratio 0.97.

EXAMPLE 5

The procedure of Example 1 was repeated. However, 0.0050 part by weight of the co-catalyst of the formula

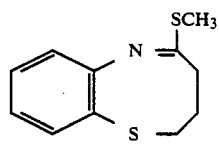

(5-methylthio-3,4-dihydro-2H-1,6-benzothiazocine)

was added. The residual toluene content was 3.5% by weight and the o/p ratio 0.93.

EXAMPLE 6

The procedure of Example 1 was repeated. However, 0.0055 part by weight of the co-catalyst of the formula

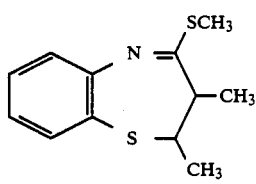

(2,3-dimethyl-4-methylthio-2,3-dihydro-1,5-benzothiazepine)

was added. The residual toluene content was 4.1% by weight and the o/p ratio 0.66.

EXAMPLE 7

The procedure of Example 1 was repeated. However, 0.0059 part by weight of the co-catalyst of the formula

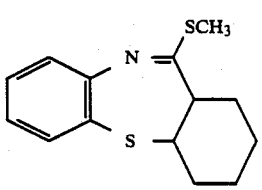

(2,3-tetramethylene-4-methylthio-2,3-dihydro-1,5-benzothiazepine)

was added. The residual toluene content was 4.0% by weight and the o/p ratio 0.63.

EXAMPLE 8

The procedure of Example 1 was repeated. However, 100 parts by weight of ethylbenzene were used and 0.0060 part by weight of the co-catalyst of Example 7 was added. The residual ethylbenzene content was 10.7% by weight; the ratio of ortho-chloroethylbenzene to parachloroethylbenzene was 0.47.

EXAMPLE 9

The procedure of Example 1 was repeated. However, 100 parts by weight of isopropylbenzene were used and 0.0060 part by weight of the co-catalyst of Example 7 was added. The residual isopropylbenzene content was 10.9% by weight; the ratio of ortho-chloroisopropylbenzene to parachloroisopropylbenzene was 0.24.

EXAMPLE 10

The procedure of Example 1 was repeated. However, 100 parts by weight of t-butylbenzene were used and 0.0059 part by weight of the co-catalyst of Example 7 was added. The residual t-butylbenzene content was 9.4% by weight; the ratio of ortho-chloro-t-butylbenzene to parachloro-t-butylbenzene was 0.11.

EXAMPLE 11

The procedure of Example 1 was repeated. However, 100 parts by weight of cyclohexylbenzene were used and 0.0055 part by weight of the co-catalyst of Example 6 was added. The residual cyclohexylbenzene content was 10.57% by weight; the ratio of ortho-chlorocyclohexylbenzene to parachlorocyclohexylbenzene was 0.23.

EXAMPLE 12

The procedure of Example 1 was repeated. However, 0.0059 part by weight of the co-catalyst of the formula

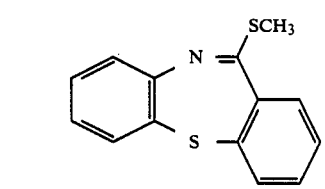

(4-methylthio-1,5-dibenzo-[b,f]thiazepine)

was added. The residual toluene content was 4.1% by weight and the o/p ratio 1.26.

EXAMPLE 13

The procedure of Example 1 was repeated. However, 0.0060 part by weight of the co-catalyst of the formula

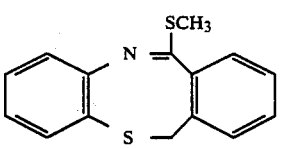

(5-methylthio-2H-1,6-dibenzo-[c,g]thiazocine)

was added. The residual toluene content was 5.1% by weight and the o/p ratio 1.16.

EXAMPLE 14

The procedure of Example 1 was repeated. However, 0.0055 part by weight of the co-catalyst of the formula

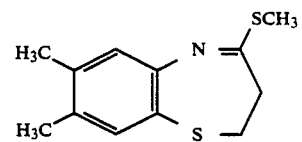

(4-methylthio-7,8-dimethyl-2,3-dihydro-1,5-benzothiazepine)

was added. The residual toluene content was 2.9% by weight and the o/p ratio 0.68.

EXAMPLE 15

The procedure of Example 1 was repeated. However, 0.0065 part by weight of the co-catalyst of the formula

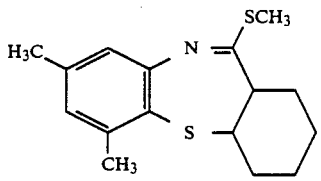

(7,9-dimethyl-4-methylthio-2,3-tetramethylene-2,3-dihydro-1,5-benzothiazepine)

was added. The residual toluene content was 3.7% by weight and the o/p ratio 0.55.

EXAMPLE 16

The procedure of Example 1 was repeated. However, 0.0055 part by weight of the co-catalyst of the formula

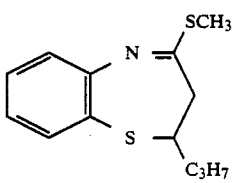

(2-propyl-4-methylthio-2,3-dihydro-1,5-benzothiazepine)

was added. The residual toluene content was 2.8% by weight and the o/p ratio 0.69.

EXAMPLE 17

The procedure of Example 1 was repeated. However, 0.0064 part by weight of the co-catalyst of the formula

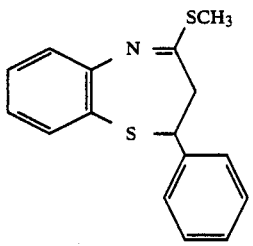

(2-phenyl-4-methylthio-2,3-dihydro-1,5-benzothiazepine)

was added. The residual toluene content was 4.7% by weight and the o/p ratio 1.06.

EXAMPLE 18

The procedure of Example 1 was repeated. However, 0.0062 part by weight of the co-catalyst of the formula

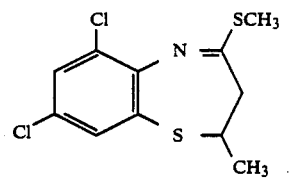

(6,8-dichloro-4-methylthio-2,3-dihydro-1,5-benzothiazepine)

was added. The residual toluene content was 3.75% by weight and the o/p ratio 0.91.

EXAMPLE 19

The procedure of Example 1 was repeated. However, 0.0061 part by weight of the co-catalyst of the formula

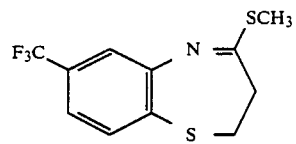

(7-trifluoromethyl-4-methylthio-2,3-dihydro-1,5-benzothiazepine)

was added. The residual toluene content was 4.8% by weight and the o/p ratio 0.84.

EXAMPLE 20

The procedure of Example 1 was repeated. However, 0.0052 part by weight of the co-catalyst of the formula

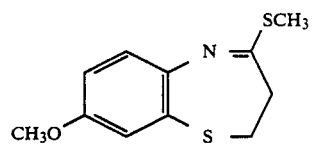

(8-methoxy-4-methylthio-2,3-dihydro-1,5-benzothiazepine)

was added. The residual toluene content was 2.1% by weight and the o/p ratio 0.78.

EXAMPLE 21

The procedure of Example 1 was repeated. However, 0.0045 part by weight of the co-catalyst of the formula

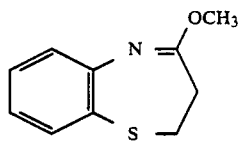

(4-methoxy-2,3-dihydro-1,5-benzothiazepine)

was added. The residual toluene content was 3.9% by weight and the o/p ratio 0.71.

EXAMPLE 22

The procedure of Example 1 was repeated. However, 0.0065 part by weight of the co-catalyst of the formula

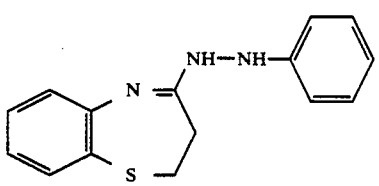

(4-phenylhydrazino-2,3-dihydro-1,5-benzothiazepine)

EXAMPLE 23

The procedure of Example 1 was repeated. However, 0.0040 part by weight of the co-catalyst of the formula

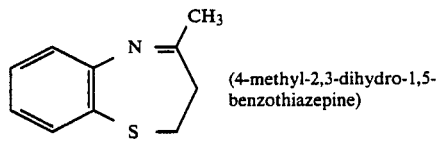
(4-methyl-2,3-dihydro-1,5-benzothiazepine)

was added. The residual toluene content was 3.7% by weight and the o/p ratio 0.75.

EXAMPLE 24

The procedure of Example 1 was repeated. However, 0.0045 part by weight of the co-catalyst of the formula

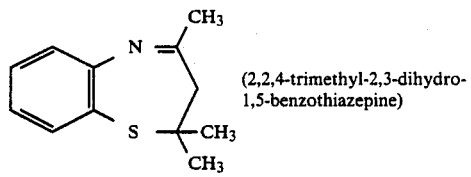
(2,2,4-trimethyl-2,3-dihydro-1,5-benzothiazepine)

was added. The residual toluene content was 4.5% by weight and the o/p ratio 1.00.

EXAMPLE 25

The procedure of Example 1 was repeated. However, 0.0050 part by weight of the co-catalyst of the formula

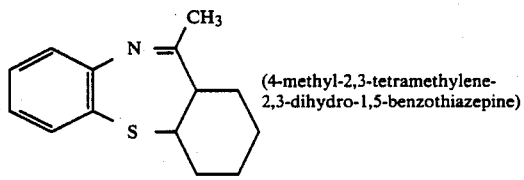
(4-methyl-2,3-tetramethylene-2,3-dihydro-1,5-benzothiazepine)

was added. The residual toluene content was 3.4% by weight and the o/p ratio 0.68.

EXAMPLE 26

A solution consisting of 100 parts by weight of toluene, 0.017 part by weight of FeCl₃ and 0.0055 part by weight of the co-catalyst from Example 7 was prepared at room temperature. This solution was introduced into a chlorination reactor operating continuously at 40° to 45° C., while simultaneously removing the equivalent amount of chlorination product. Gaseous chlorine was added as a chlorinating agent at such a rate that the conversion remained largely constant at about 94 mol %. The removed chlorination mixture contained about 7.5% by weight of toluene. The ratio of orthochlorotoluene to para-chlorotoluene was 0.63.

EXAMPLE 27 (COMPARATIVE EXAMPLE)

0.07 part by weight of FeCl₃ and 0.29 part by weight of the phenoxathiine derivative prepared according to EP No. 0,173,222 were dissolved in 100 parts by weight of toluene. At 50° C., about 94 mol % of chlorine were introduced in the form of a gas with stirring. The residual content of toluene was 7.9% and the o/p ratio 0.88.

EXAMPLE 28 (COMPARATIVE EXAMPLE)

The procedure of Example 27 was repeated. 0.017 part by weight of FeCl₃ and 0.008 part by weight of the phenoxathiine derivative prepared according to EP No. 0,173,222 were dissolved in 100 parts by weight of toluene. At 50° C., about 94 mol % of Cl₂ were introduced in the form of a gas with stirring. The residual toluene content was 6.4% by weight and the o/p ratio 1.26.

EXAMPLE 29 (COMPARATIVE EXAMPLE)

The procedure of Example 27 was repeated. 0.017 part by weight of FeCl₃ and 0.0065 part by weight of the co-catalyst of the formula

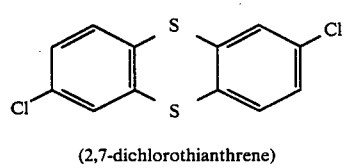
(2,7-dichlorothianthrene)

mentioned in Example 4, of U.S. Pat. No. 4,031,147, were dissolved in 100 parts by weight of toluene. The mixture was heated to 50° C., and about 94 mol % of Cl₂ were introduced in the form of a gas with stirring. The residual toluene content was 6.7% by weight and the o/p ratio 1.55.

EXAMPLE 30 (COMPARATIVE EXAMPLE)

The procedure of Example 27 was repeated. 0.017 part by weight of FeCl₃ and 0.006 part by weight of the co-catalyst of the formula

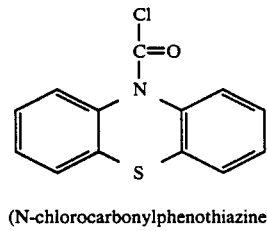
(N-chlorocarbonylphenothiazine)

mentioned in Example 1 of EP No. 0,126,669 were dissolved in 100 parts by weight of toluene. The mixture was heated to 50° C., and about 94 mol % of chlorine were introduced in the form of a gas with stirring. The residual toluene content was 5.6% by weight and the o/p ratio 1.04.

EXAMPLE 31

100 parts by weight of toluene were initially introduced into a reactor with stirring, 0.017 part by weight of FeCl₃ and 0.0050 part by weight of the co-catalyst of the formula

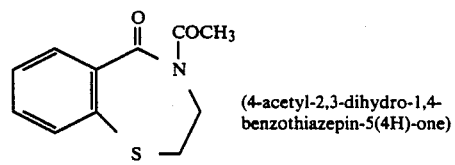
(4-acetyl-2,3-dihydro-1,4-benzothiazepin-5(4H)-one)

were added, and the mixture was heated to 50° C. While maintaining the temperature essentially constant (±1° C.) about 94 mol % of chlorine (based on alkylbenzene) were uniformly added as a gas over a period of 5 hours. The residual toluene content in the reaction mixture was 3.0% by weight and the ratio of ortho-chlorotoluene to para-chlorotoluene (o/p) was 0.71.

EXAMPLE 32

The procedure of Example 1 was repeated. However, 0.0043 part by weight of the co-catalyst of the formula

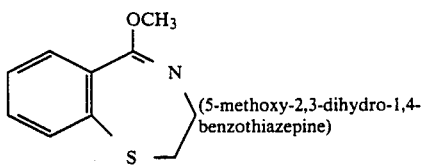

was added. The residual toluene content was 4.0% by weight and the o/p ratio 0.83.

EXAMPLE 33

The procedure of Example 1 was repeated. However, 0.0049% by weight of the co-catalyst of the formula

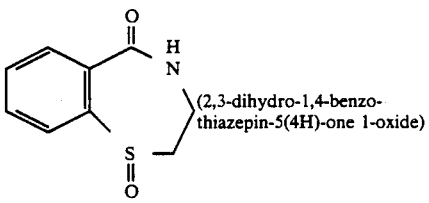

was added. The residual toluene content was 3.1% by weight and the o/p ratio 0.70.

EXAMPLE 34

The procedure of Example 1 was repeated. However, 0.0045% by weight of the co-catalyst of the formula

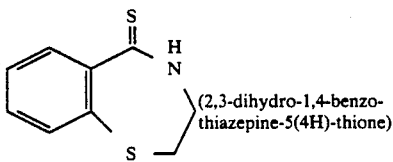

was added. The residual toluene content was 3.2% by weight and the o/p ratio 0.74.

EXAMPLE 35

The procedure of Example 1 was repeated. However, 0.0045% by weight of the co-catalyst of the formula

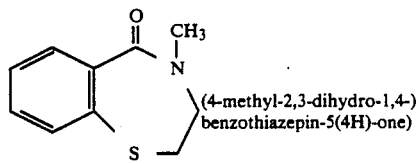

was added. The residual toluene content was 3.5% by weight and the o/p ratio 0.73.

EXAMPLE 36

The procedure of Example 1 was repeated. However, 0.0045% by weight of the co-catalyst of the formula

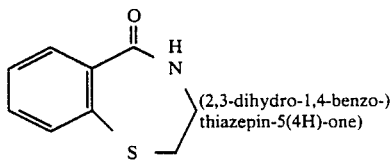

was added. The residual toluene content was 3.3% by weight and the o/p ratio 0.71.

EXAMPLE 37

The procedure of Example 1 was repeated. However, 0.0042% by weight of the co-catalyst of the formula

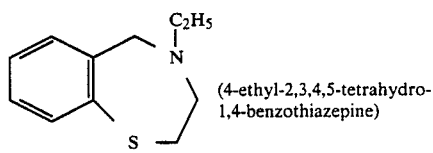

was added. The residual toluene content was 4.0% by weight and the o/p ratio 0.81.

EXAMPLE 38

The procedure of Example 1 was repeated. However, 0.0065% by weight of the co-catalyst of the formula

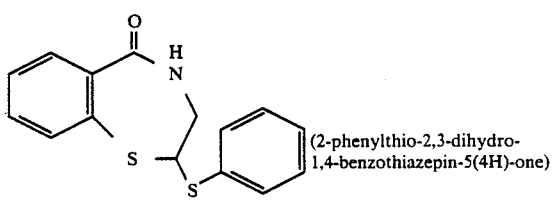

was added. The residual toluene content was 4.0% by weight and the o/p ratio 1.00.

EXAMPLE 39

The procedure of Example 1 was repeated. However, 0.0048% by weight of the co-catalyst of the formula

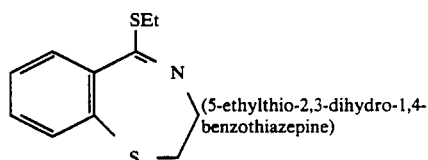

was added. The residual toluene content was 3.6% by weight and the o/p ratio 0.80.

EXAMPLE 40

The procedure of Example 1 was repeated. However, 0.0049% by weight of the co-catalyst of the formula

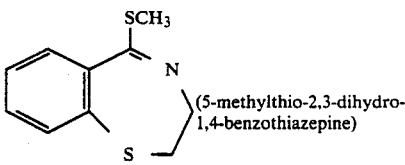

(5-methylthio-2,3-dihydro-1,4-benzothiazepine)

was added. The residual toluene content was 4.1% by weight and the o/p ratio 0.76.

EXAMPLE 41

The procedure of Example 1 was repeated. However, 0.0064% by weight of the co-catalyst of the formula

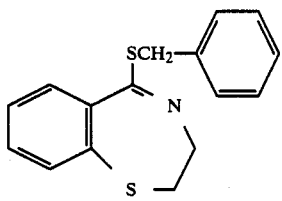

(5-benzylthio-2,3-dihydro-1,4-benzothiazepine)

was added. The residual toluene content was 3.4% by weight and the o/p ratio 0.71.

EXAMPLE 42

The procedure of Example 1 was repeated. However, 0.0060% by weight of the co-catalyst of the formula

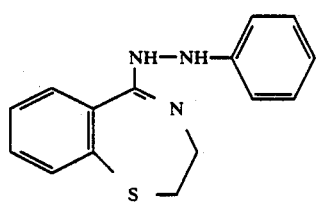

(5-β-phenylhydrazino-2,3-dihydro-1,4-benzothiazepine)

was added. The residual toluene content was 4.3% by weight and the o/p ratio 0.64.

EXAMPLE 43

The procedure of Example 1 was repeated. However, 0.0048% by weight of the co-catalyst of the formula

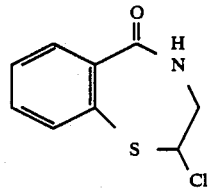

(2-chloro-2,3-dihydro-1,4-benzothiazepin-5(4H)-one)

was added and the mixture was heated to 52°-53° C. The residual toluene content was 4.1% by weight and the o/p ratio 0.73.

EXAMPLE 44

The procedure of Example 1 was repeated. However, 0.0045% by weight of the co-catalyst of the formula

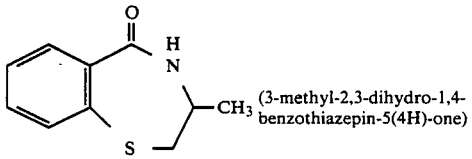

(3-methyl-2,3-dihydro-1,4-benzothiazepin-5(4H)-one)

was added and the mixture was heated to 50°-52° C. The residual toluene content was 3.0% by weight and the o/p ratio 0.69.

EXAMPLE 45

The procedure of Example 1 was repeated. However, 0.0044% by weight of the co-catalyst of the formula

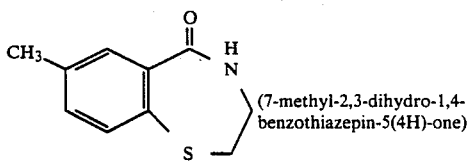

(7-methyl-2,3-dihydro-1,4-benzothiazepin-5(4H)-one)

was added. The residual toluene content was 2.9% by weight and the o/p ratio 0.68.

EXAMPLE 46

The procedure of Example 1 was repeated. However, 0.0045% by weight of the co-catalyst of the formula

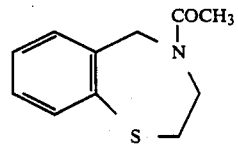

(4-acetyl-2,3,4,5-tetrahydro-1,4-benzothiazepine)

was added. The residual toluene content was 2.9% by weight and the o/p ratio 0.93.

EXAMPLE 47

The procedure of Example 1 was repeated. However, 0.0047% by weight of the co-catalyst of the formula

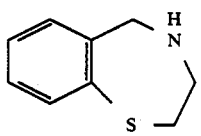

(2,3,4,5-tetrahydro-1,4-benzothiazepine)

was added. The residual toluene content was 4.3% and the o/p ratio 0.88.

EXAMPLE 48

The procedure of Example 1 was repeated. However, 100 parts by weight of ethylbenzene were used and 0.0043 part by weight of the co-catalyst of Example 15 was added. The residual ethylbenzene content was 4.6% by weight; the ratio of ortho-chloroethylbenzene to para-chloroethylbenzene was 0.50.

EXAMPLE 49

The procedure of Example 1 was repeated. However, 100 parts by weight of isopropylbenzene were used and 0.0040 part by weight of the co-catalyst of Example 6 was added. The residual isopropylbenzene content was 5.0% by weight; the ratio of ortho-chloroisopropylbenzene to para-chloroisopropylbenzene was 0.25.

EXAMPLE 50

The procedure of Example 1 was repeated. However, 100 parts by weight of t-butylbenzene were used and 0.0042 part by weight of the co-catalyst of Example 14 was added. The residual t-butylbenzene content was 5.2% by weight; the ratio of ortho-chloro-tert-butylbenzene to para-chloro-tert-butylbenzene was 0.16.

EXAMPLE 51

The procedure of Example 1 was repeated. However, 100 parts by weight of cyclohexylbenzene were used and 0.0042 part by weight of the co-catalyst of Example 5 was added. The residual cyclohexylbenzene content was 5.5% by weight; the ratio of ortho-chlorocyclohexylbenzene to chlorocyclohexylbenzene was 0.22.

EXAMPLE 52

The procedure of Example 1 was repeated. However, 0.0050 part by weight of a potassium salt of the following formula

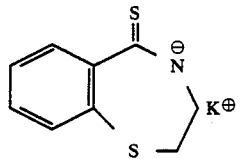

(2,3-dihydro-1,4-benzothiazepin-5(4H)-thione, K salt), which during the chlorination is converted into the co-catalyst of Example 4. The residual toluene content was 3.8% by weight and the o/p ratio 0.73.

EXAMPLE 53

The procedure of Example 1 was repeated. However, 0.0055 part by weight of the co-catalyst of the formula

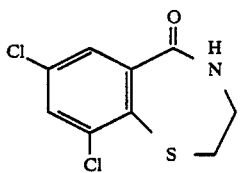

(7,9-dichloro-2,3-dihydro-1,4-benzothiazepin-5(4H)-one)

was added. The residual toluene content was 4.5% by weight and the o/p ratio 0.74.

EXAMPLE 54

The procedure of Example 1 was repeated. However, 0.0050 part by weight of the co-catalyst of the formula

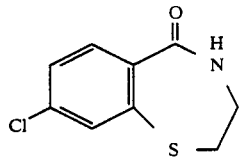

(8-chloro-2,3-dihydro-1,4-benzothiazepin-5(4H)-one)

was added. The residual toluene content was 3.8% by weight and the o/p ratio 0.74.

EXAMPLE 55

The procedure of Example 1 was repeated. However, 0.0048 part by weight of the co-catalyst of the formula

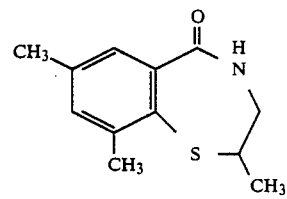

(2,7,9-trimethyl-2,3-dihydro-1,4-benzothiazepin-5(4H)-one)

was added. The residual toluene content was 4.9% by weight and the o/p ratio 0.66.

EXAMPLE 56

The procedure of Example 1 was repeated. However, 0.0055 part by weight of the co-catalyst of the formula

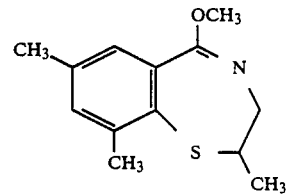

(2,7,9-trimethyl-5-methoxy-2,3-dihydro-1,4-benzothiazepine)

was added. The residual toluene content was 3.0% by weight and the o/p ratio 0.66.

EXAMPLE 57

The procedure of Example 1 was repeated. However, 0.00073 part by weight of the co-catalyst of the formula

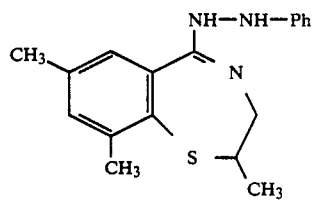

(2,7,9-trimethyl-5-β-phenylhydrazino-2,3-dihydro-1,4-benzothiazepine)

was added. The residual toluene content was 3.3% by weight and the o/p ratio 0.65.

What is claimed is:

1. A process for the ring chlorination of aromatic hydrocarbons of the formula

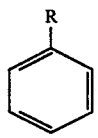

in which
R denotes straight-chain or branched $C_1$-$C_{12}$-alkyl or $C_3$-$C_8$-cycloalkyl in the presence of Friedel-Crafts catalysts and in the presence of co-catalysts in liquid phase, wherein the chlorinating agent is selected from the group comprising chlorine and sulphur chloride, at a reaction temperature of from about zero to about 100° C., and wherein the co-catalysts used are cycloicbenzo-fused imines of the formula

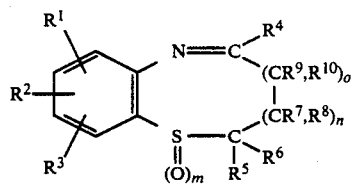

in which
$R^1$ and $R^2$, independently of one another, denote hydrogen, hydroxyl, amino, cyano, halogen, nitro, carboxyl, halocarbonyl, carboxyamide, alkoxycarbonyl, alkyl, aryl, alkoxy, aryloxy, acyloxy, alkylthio, arylthio, acylthio, acyl, thioacyl or acylamino, $R^3$ represents hydrogen or chlorine and can be a fused saturated, unsaturated or aromatic isocyclic or heterocyclic 5- to 8-membered ring with one of the radicals $R^1$ and $R^2$, when substituted adjacently, and together with the substituted carbon atoms, $R^4$ denotes hydrogen, alkyl, aryl, halogen, alkylthio, arylthio, alkoxy, aryloxy amino, hydrazino, alkylhydrazino or phenylhydrazino, m, n and o, independently of one another are 0 or 1 and $R^5$, $R^7$ and $R^9$, independently of one another, denote hydrogen, alkyl, alkoxy, phenyl, acyloxy, cyano, halogen, carboxyl, alkoxycarbonyl, phenoxy or acyl and $R^6$, $R^8$ and $R^{10}$, independently of one another denote hydrogen, alkyl or halogen, $R^5$ and $R^7$ or $R^7$ and $R^9$ can be a saturated, unsaturated or aromatic isocyclic or heterocyclic 5–8-membered ring together with the substituted C atoms and $R^6$ and $R^8$ or $R^8$ and $R^{10}$ together can form a double bond and $R^5$ and $R^6$ can represent together doubly bound oxygen, sulphur, or $R^{11}$-substituted nitrogen in which $R^{11}$ denotes alkyl, aryl, acyl, alkylamino or arylamino, or benzo[f]-1,4-thiazepines of the formula

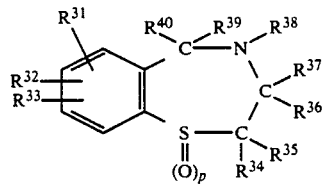

in which
$R^{31}$ and $R^{32}$, independently of one another, denote hydrogen, hydroxyl, amino, cyano, halogen, nitro, $C_1$-$C_8$-alkyl, unsubstituted or $R^{31}$- and $R^{32}$-substituted phenyl (with the exception of repeated substitution by $R^{31}$- and $R^{32}$-substituted phenyl), $C_1$-$C_8$-alkoxy, phenoxy, $C_1$-$C_8$-acyloxy, $C_1$-$C_8$-acyl or $C_1$-$C_8$-alkoxycarbonyl, $R^{33}$ represents hydrogen or chlorine and can be a fused saturated, unsaturated or aromatic isocyclic or heterocyclic 5–8-membered ring with one of the radicals $R^{31}$ or $R^{32}$ and together with the substituted C atoms, $R^{34}$, $R^{36}$ and $R^{40}$, independently of one another, denote hydrogen, $C_1$-$C_8$-alkyl, unsubstituted or $R^{31}$-and $R^{32}$-substituted phenyl (with the exception of repeated substitution by $R^{31}$- and $R^{32}$-substituted phenyl), $C_1$-$C_8$-acyl, $C_1$-$C_8$-alkoxycarbonyl, cyano, halogen, carboxyl, $C_1$-$C_8$-alkoxy, $C_1$-$C_8$-alkylthio, phenylthio, benzylthio, phenoxy or $C_1$-$C_8$-acyloxy, $R^{35}$, $R^{37}$ and $R^{39}$, independently of one another, denote hydrogen, $C_1$-$C_8$-alkyl, halogen, $C_1$-$C_8$-alkoxy or $C_1$-$C_8$-alkylthio, $R^{38}$ denotes hydrogen, $C_1$-$C_8$-alkyl, unsubstituted or $R^{31}$-and $R^{32}$-substituted phenyl (with the exception of repeated substitution by $R^{31}$- and $R^{32}$-substituted phenyl), $C_1$-$C_8$-acyl, $C_1$-$C_8$-thioacyl, halogenocarbonyl or $C_1$-$C_8$-alkoxycarbonyl and P represents the number zero or one, the substituent pairs $R^{34}$ and $R^{35}$, $R^{36}$ and $R^{37}$, and $R^{39}$ and $R^{40}$, independently of one another, can be doubly bound oxygen, sulphur or $R^{38}$-substituted nitrogen and the substituent pairs $R^{35}$ and $R^{36}$ and $R^{38}$ and $R^{39}$, independently of one another, can be a double bond and the substituent pairs $R^{34}$ and $R^{37}$, and $R^{38}$ and $R^{39}$, independently of one another, can be 3-to 5-membered alkylene in which 1 or 2 C atoms can be replaced by oxygen, sulphur or $R^{38}$-substituted nitrogen and $R^{40}$ can be hydrazino, $C_1$-$C_8$-alkylhydrazino or phenylhydrazino.

2. The process of claim 1, wherein cyclic benzo-fused imines of the formulae

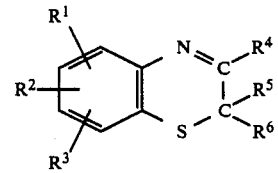

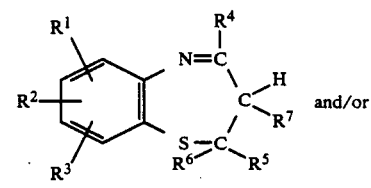

and/or

-continued

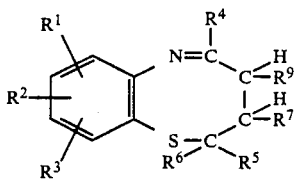

are used in which $R^1$ to $R^9$ have the range of meanings mentioned in claim 1.

3. The process of claim 2, wherein the radicals $R^{12}$, $R^{13}$ and $R^{14}$ take the place of $R^1$, $R^2$ and $R^3$, of which $R^{12}$ and $R^{13}$, independently of one another, denote hydrogen, halogen, nitro, alkyl, aryl, alkoxy, aryloxy, acyloxy, alkylthio, arylthio, acyl or thioacyl and $R^{14}$ represents hydrogen or chlorine and furthermore can form a fused, saturated isocyclic 5-7-membered ring or a fused benzene ring with one of the radicals $R^{12}$ and $R^{13}$ and together with the C atoms substituted by them.

4. The process of claim 3, wherein the radicals $R^{21}$, $R^{22}$ and $R^{23}$ take the place of $R^{12}$, $R^{13}$ and $R^{14}$, of which $R^{21}$ and $R^{22}$, independently of one another, denote hydrogen, $C_1$-$C_4$-alkyl, $C_1$-$C_4$-alkoxy, fluorine or chlorine and $R^{23}$ represents hydrogen or chlorine and can be a fused cyclopentane, cyclohexane or benzene ring with one of the radicals $R^{21}$ or $R^{22}$ and together with the C atoms substituted by them.

5. The process of claim 2, wherein the radical $R^{15}$ takes the place of $R^4$ and denotes hydrogen, $C_1$-$C_4$-alkyl, $C_1$-$C_4$-alkoxy, phenyl, benzyl, chlorine, $C_1$-$C_4$-acyl, $C_1$-$C_4$-alkylthio, benzyloxy, benzylthio, hydrazino, $C_1$-$C_4$-alkylhydrazino or phenylhydrazino.

6. The process of claim 5 wherein the radical $R^{24}$ takes the place of $R^{15}$ and denotes hydrogen, $C_1$-$C_4$-alkyl, benzyl, phenyl, $C_1$-$C_4$-alkoxy, $C_1$-$C_4$-alkylthio, benzyloxy, benzylthio, hydrazino or phenylhydrazino.

7. The process of claim 2, wherein the radicals $R^{16}$, $R^{17}$, $R^{18}$ and $R^{19}$ take the place of $R^5$, $R^6$, $R^7$ and $R^9$ and, independently of one another, denote hydrogen, $C_1$-$C_4$-alkyl, fluorine or chlorine, $R^{16}$, $R^{18}$ and $R^{19}$ can be $C_1$-$C_4$-alkoxy, $C_1$-$C_4$-acyl or phencyl and if substituted adjacently, can be a cyclopentane, cyclohexane or benzene ring together with the substituted C atoms.

8. The process of claim 2, wherein cyclic benzo-fused imines of the formula

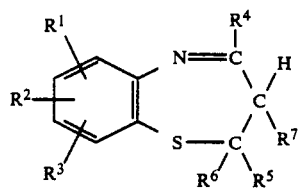

are used in which $R^1$ to $R^7$ have the range mentioned in claim 2.

9. The process of claim 1, wherein the co-catalysts used are benzo[f]-1,4-thiazepines of the formula

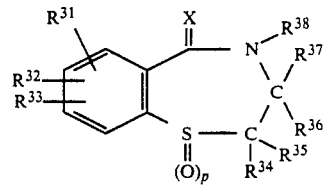

in which
X denotes doubly bound oxygen, sulphur or $R^{38}$-substituted nitrogen and
$R^{31}$, $R^{32}$, $R^{33}$, $R^{34}$, $R^{35}$, $R^{36}$, $R^{37}$, $R^{38}$ and p have the range of meanings mentioned in claim 1.

10. The process of claim 1, wherein co-catalysts of the formula

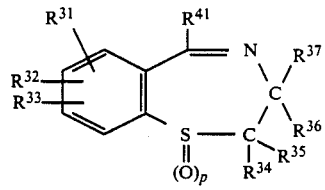

are used in which
$R^{41}$ represents $C_1$-$C_8$-alkyl, $C_1$-$C_8$-alkoxy, $C_1$-$C_8$-alkylthio, hydrazino, $\beta$-phenylhydrazino or $\beta$-$C_1$-$C_8$alkylhydrazino and
$R^{31}$, $R^{32}$, $R^{33}$, $R^{34}$, $R^{35}$, $R^{36}$, $R^{37}$ and p have the range of meanings mentioned in claim 1.

11. The process of claim 1, wherein co-catalysts of the formula

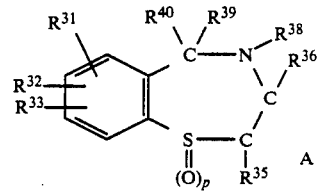

are used in which
A denotes trimethylene, tetramethylene or pentamethylene and
$R^{31}$, $R^{32}$, $R^{33}$, $R^{35}$, $R^{36}$, $R^{38}$, $R^{39}$, $R^{40}$ and p have the range of meanings mentioned in claim 1.

12. The process of claim 1, wherein p is zero.

13. The process of claim 1, wherein the radicals $R^{42}$, $R^{43}$ and $R^{44}$ take the place of $R^{31}$, $R^{32}$ and $R^{33}$, of which $R^{42}$ and $R^{43}$, independently of one another, are hydrogen, halogen, nitro, alkyl, aryl, alkoxy, aryloxy, acyloxy, alkylthio, arylthio, acyl or thioacyl and $R^{44}$ represents hydrogen or chlorine and can be a fused saturated isocyclic 5-7-membered ring or a fused benzene ring with one of the radicals $R^{42}$ and $R^{43}$ and together with the substituted C atoms.

14. The process of claim 13, wherein the radicals $R^{51}$, $R^{52}$ and $R^{53}$ take the place of $R^{42}$, $R^{43}$ and $R^{44}$, of which
$R^{51}$ and $R^{52}$, independently of one another, denote hydrogen, $C_1$-$C_4$-alkyl, $C_1$-$C_4$-alkoxy, fluorine or chlorine and
$R^{53}$ represents hydrogen or chlorine and furthermore can form a fused cyclopentane, cyclohexane or benzene ring with one of the radicals $R^{51}$ or $R^{52}$ and together with the substituted C atoms.

15. The process of claim 1, wherein the amount of co-catalyst used is 0.0001–0.5% by weight, relative to the aromatic hydrocarbon used.

16. The process of claim 15, wherein the amount of co-catalyst used is 0.0005–0.1% by weight, relative to the aromatic hydrocarbon used.

17. The process of claim 16, wherein the amount of co-catalyst used is 0.0005–0.0075% by weight, relative to the aromatic hydrocarbon used.

* * * * *